(12) United States Patent
Harris et al.

(10) Patent No.: US 11,259,883 B2
(45) Date of Patent: Mar. 1, 2022

(54) ROBOTICS TOOL EXCHANGE

(71) Applicant: Ethicon LLC, Guaynabo, PR (US)

(72) Inventors: Jason L. Harris, Lebanon, OH (US); Michael J. Vendely, Lebanon, OH (US); Nichole Y. Kwee, Cincinnati, OH (US); Frederick E. Shelton, IV, Hillsboro, OH (US)

(73) Assignee: CILAG GMBH IN TERNATIONAL, Zug (CH)

( * ) Notice: Subject to any disclaimer, the term of this patent is extended or adjusted under 35 U.S.C. 154(b) by 40 days.

(21) Appl. No.: 16/905,835

(22) Filed: Jun. 18, 2020

(65) Prior Publication Data

US 2020/0315718 A1    Oct. 8, 2020

Related U.S. Application Data

(63) Continuation of application No. 15/238,124, filed on Aug. 16, 2016, now Pat. No. 10,687,904.

(51) Int. Cl.
| | |
|---|---|
| *A61B 34/30* | (2016.01) |
| *A61B 17/34* | (2006.01) |
| *A61B 34/35* | (2016.01) |
| *A61B 34/00* | (2016.01) |
| *A61B 34/20* | (2016.01) |
| *A61B 17/00* | (2006.01) |

(Continued)

(52) U.S. Cl.
CPC ........ *A61B 34/30* (2016.02); *A61B 17/07292* (2013.01); *A61B 17/3421* (2013.01); *A61B 17/3462* (2013.01); *A61B 34/35* (2016.02); *A61B 50/20* (2016.02); *A61B 50/22* (2016.02); *A61B 50/36* (2016.02); *A61B 90/70* (2016.02); *A61B 50/30* (2016.02); *A61B 2017/00477* (2013.01); *A61B 2017/00876* (2013.01); *A61B 2017/07271* (2013.01); *A61B 2017/3409* (2013.01); *A61B 2034/2051* (2016.02); *A61B 2034/741* (2016.02); *A61B 2034/742* (2016.02); *A61B 2090/0808* (2016.02); *A61B 2090/0811* (2016.02)

(58) Field of Classification Search
CPC ..... A61B 34/30; A61B 34/35; A61B 17/3421; A61B 2034/2051; A61B 2017/00477; B25J 15/0466
See application file for complete search history.

(56) References Cited

U.S. PATENT DOCUMENTS

| | | | |
|---|---|---|---|
| 4,441,746 | A | 4/1984 | Corboy, Jr. |
| 5,441,042 | A | 8/1995 | Putman |

(Continued)

OTHER PUBLICATIONS

U.S. Appl. No. 15/238,124, filed Aug. 16, 2016, Robotics Tool Exchange.

(Continued)

*Primary Examiner* — Nathan J Jenness
(74) *Attorney, Agent, or Firm* — Mintz Levin Cohn Ferris Glovsky and Popeo, P. C.

(57) ABSTRACT

An electromechanical robotic arm is provided having a distal end with a tool engaging member configured to mate with an electromechanical tool and a trocar holding member configured to mate with a trocar. The trocar holding member can have at least one engagement mechanism configured to engage and orient a trocar to mate the trocar to the trocar holding member in a desired orientation.

16 Claims, 10 Drawing Sheets

(51) Int. Cl.
*A61B 17/072* (2006.01)
*A61B 50/36* (2016.01)
*A61B 90/70* (2016.01)
*A61B 50/20* (2016.01)
*A61B 50/22* (2016.01)
*A61B 90/00* (2016.01)
*A61B 50/30* (2016.01)

(56) References Cited

U.S. PATENT DOCUMENTS

| | | |
|---|---|---|
| 6,279,885 B1 | 8/2001 | Leon, Jr. |
| 8,114,345 B2 | 2/2012 | Dlugos, Jr. et al. |
| 8,827,216 B2 | 9/2014 | Brown et al. |
| 8,882,792 B2 | 11/2014 | Dietz et al. |
| 8,915,842 B2 | 12/2014 | Weisenburgh, II et al. |
| 8,931,682 B2 | 1/2015 | Timm et al. |
| 8,945,098 B2 | 2/2015 | Seibold et al. |
| 2003/0208187 A1 | 11/2003 | Layer |
| 2007/0151389 A1 | 7/2007 | Prisco et al. |
| 2008/0081948 A1 | 4/2008 | Weisenburgh et al. |
| 2009/0202387 A1 | 8/2009 | Dlugos, Jr. et al. |
| 2009/0298658 A1 | 12/2009 | Yeh |
| 2010/0217245 A1 | 8/2010 | Prescott |
| 2011/0071473 A1* | 3/2011 | Rogers ............... A61B 17/0218 604/167.01 |
| 2011/0118709 A1 | 5/2011 | Burbank |
| 2011/0118778 A1 | 5/2011 | Burbank |
| 2013/0282052 A1 | 10/2013 | Aranyi et al. |
| 2014/0005718 A1 | 1/2014 | Shelton, IV et al. |
| 2014/0066944 A1 | 3/2014 | Taylor et al. |
| 2014/0360305 A1 | 12/2014 | Olds et al. |
| 2015/0164593 A1 | 6/2015 | Lohmeier et al. |
| 2015/0374445 A1* | 12/2015 | Gombert ............... B25J 15/0206 606/130 |
| 2016/0016320 A1 | 1/2016 | Rothfuss et al. |
| 2017/0000541 A1 | 1/2017 | Yates et al. |
| 2017/0086932 A1* | 3/2017 | Auld .................... A61B 34/71 |
| 2017/0105811 A1* | 4/2017 | Garbus ............. A61B 17/3476 |
| 2017/0296173 A1 | 10/2017 | Shelton, IV et al. |
| 2018/0049824 A1 | 2/2018 | Harris et al. |
| 2019/0290389 A1* | 9/2019 | Kopp ................ A61B 17/3462 |

OTHER PUBLICATIONS

Correlated Solutions (2013) "Principle of Digital Image Correlation", Available at: http://correlatedsolutions.com/digital-image-correlation, (5 pages).

* cited by examiner

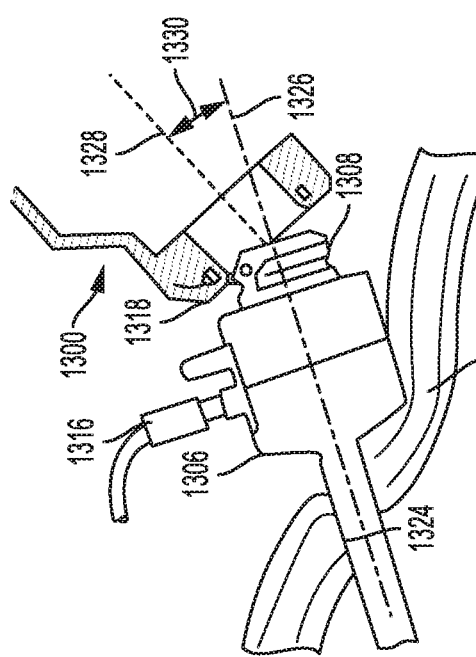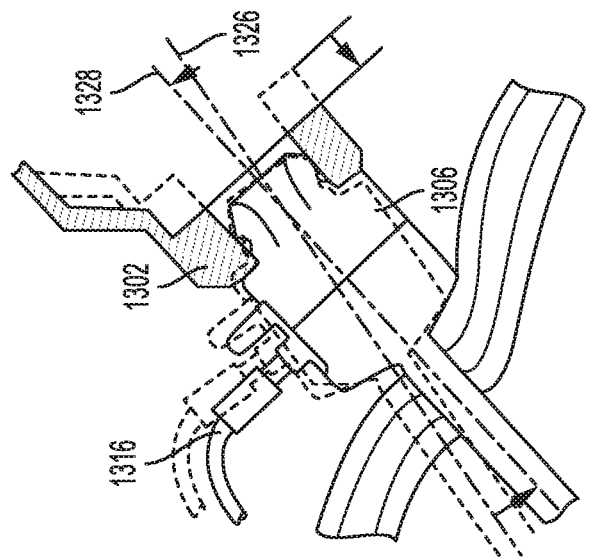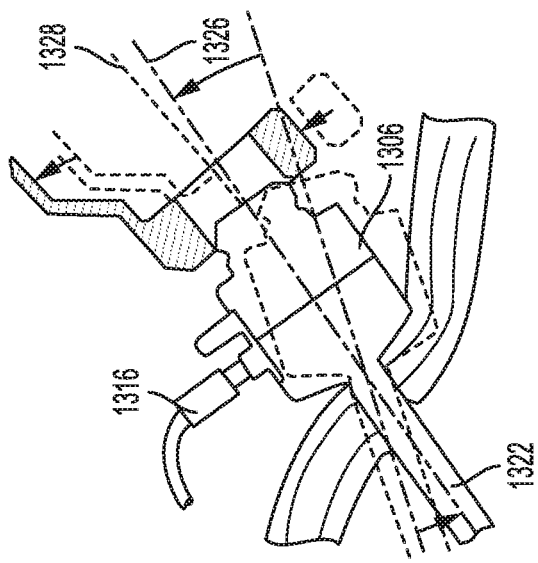
FIG. 5A
FIG. 5B
FIG. 5C

ROBOTICS TOOL EXCHANGE

CROSS-REFERENCE TO RELATED APPLICATION

This application is a continuation of U.S. application Ser. No. 15/238,124 filed on Aug. 16, 2016, entitled "Robotics Tool Exchange," which is hereby incorporated herein by its entirety.

FIELD OF THE INVENTION

Methods and devices are provided for robotic surgery, and in particular for communicating with and controlling robotic tools.

BACKGROUND OF THE INVENTION

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Although traditional minimally invasive surgical instruments and techniques have proven highly effective, newer systems may provide even further advantages. For example, traditional minimally invasive surgical instruments often deny the surgeon the flexibility of tool placement found in open surgery. Difficulty is experienced in approaching the surgical site with the instruments through the small incisions. Additionally, the added length of typical endoscopic instruments often reduces the surgeon's ability to feel forces exerted by tissues and organs on the end effector. Furthermore, coordination of the movement of the end effector of the instrument as viewed in the image on the television monitor with actual end effector movement is particularly difficult, since the movement as perceived in the image normally does not correspond intuitively with the actual end effector movement. Accordingly, lack of intuitive response to surgical instrument movement input is often experienced. Such a lack of intuitiveness, dexterity and sensitivity of endoscopic tools has been found to be an impediment in the increased the use of minimally invasive surgery.

Over the years a variety of minimally invasive robotic systems have been developed to increase surgical dexterity as well as to permit a surgeon to operate on a patient in an intuitive manner. Telesurgery is a general term for surgical operations using systems where the surgeon uses some form of remote control, e.g., a servomechanism, or the like, to manipulate surgical instrument movements, rather than directly holding and moving the tools by hand. In such a telesurgery system, the surgeon is typically provided with an image of the surgical site on a visual display, thus allowing the surgeon to view and control end effector movement by manipulating master control devices.

While significant advances have been made in the field of robotic surgery, there remains a need for improved methods, systems, and devices for use in robotic surgery.

SUMMARY OF THE INVENTION

Various robot systems and methods are provided for coupling a trocar to a robotic arm, thereby allowing for automatic tool exchange during a surgical procedure. In one embodiment, a surgical system is provided and includes an electromechanical robotic arm having a distal end with a tool engaging member configured to mate with an electromechanical tool and a trocar holding member configured to mate with a trocar. The trocar holding member can have at least one engagement mechanism configured to engage and orient a trocar to mate the trocar to the trocar holding member in a desired orientation.

In one embodiment, the trocar holding member can be configured to automatically engage a trocar when positioned in proximity to a trocar. For example, the trocar holding member can include at least one magnet configured to attract a trocar to thereby automatically engage the trocar. The at least one magnet can be, for example, an electromagnet configured to generate an electromagnetic field to attract a trocar into the trocar holding member. In certain aspects, the at least one magnet can be configured to cause rotation of the trocar within the trocar holding mechanism.

In another embodiment, the trocar holding member can be configured to automatically orient a trocar into a predetermined desired orientation when the trocar holding member is positioned in proximity to a trocar. For example, the trocar holding member can include at least one rotatable wheel disposed thereon and configured to allow rotation of a trocar engaged by the trocar holding member. In other embodiments, the trocar holding member can include at least one rotatable wheel disposed thereon and configured to rotate to cause rotation of a trocar engaged by the trocar holding member.

The trocar holding member can include other features, such as at least one sensor disposed thereon and configured to sense at least one of a location and an orientation of a trocar.

The configuration of the trocar holding member can also vary, and in one embodiment the trocar holding member can include first and second grasper arms movable between an open position configured to receive a trocar therebetween and a closed position configured to engage the trocar. The trocar holding member can in other embodiments be substantially ring-shaped or C-shaped.

In other aspects, the electromechanical robotic arm can be coupled to a controller that is configured to receive instructions from a sensor on a trocar relating to a position and orientation of the trocar, and to transmit instructions to the electromechanical robotic arm to cause the electromechanical robotic arm to orient the trocar holding member based on the position and orientation of the trocar.

In an exemplary embodiment, the trocar holding member is configured to align a stopcock on a trocar with a support arm coupled to and supporting the trocar holding member.

Methods for coupling a robotic arm to a trocar are also provided and in one embodiment the method includes actuating a robotic system to cause an electromechanical robotic arm to position a trocar holding member in proximity to a trocar, the trocar holding member orienting the trocar in a predetermined orientation relative to the trocar holding member. The trocar holding member can also automatically acquire and engage the trocar when the trocar holding member is positioned in proximity to the trocar.

In one aspect, the trocar holding member includes at least one magnet that attracts a ferromagnetic material on the trocar to automatically acquire and engage the trocar. In other aspects, the trocar holding member can detect a location of the trocar. In another embodiment, the trocar holding member can actuate at least one rotatable wheel to orient the trocar into the predetermined orientation.

In yet another embodiment, when the trocar holding member is positioned in proximity to the trocar, pivoting arms on the trocar holding member can move from an open position to a closed position to engage the trocar within the trocar holding member. In other aspects, the trocar holding member includes at least one magnet that orients the trocar into the predetermined orientation. In another embodiment, the trocar holding member engages the trocar when the trocar holding member is positioned in proximity to the trocar, and a cam mechanism on the trocar holding member locks the trocar therein.

BRIEF DESCRIPTION OF THE DRAWINGS

The invention will be more fully understood from the following detailed description taken in conjunction with the accompanying drawings, in which:

FIG. 5A is a perspective view of the trocar holding member of FIG. 3C shown positioned at an angle relative to a trocar positioned on its side along the tissue surface;

FIG. 5B is a perspective view of the trocar holding member and trocar of FIG. 5A, with the trocar pivoted up toward the trocar holding member and away from the tissue surface;

FIG. 5C is a perspective view of the trocar mated to the trocar holding member of FIG. 5B;

DETAILED DESCRIPTION OF THE INVENTION

Figure 1:
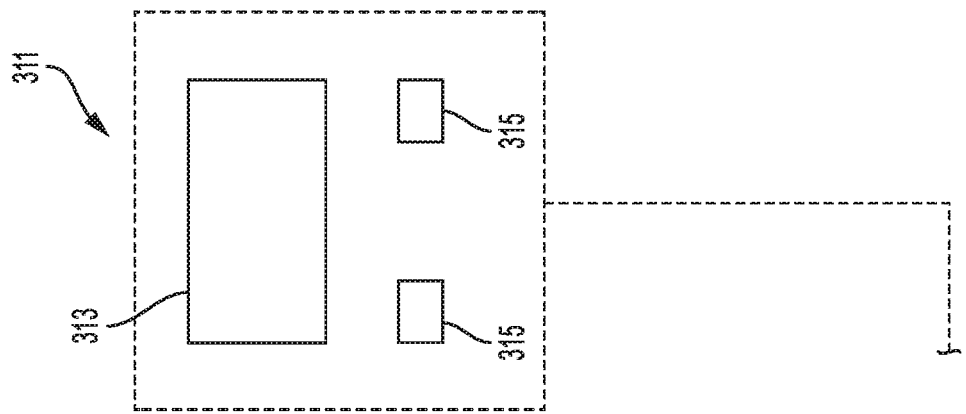
FIG. 1 is a perspective view of one embodiment of a surgical robotic system that includes a patient-side portion and a user-side portion.
Figure 1:
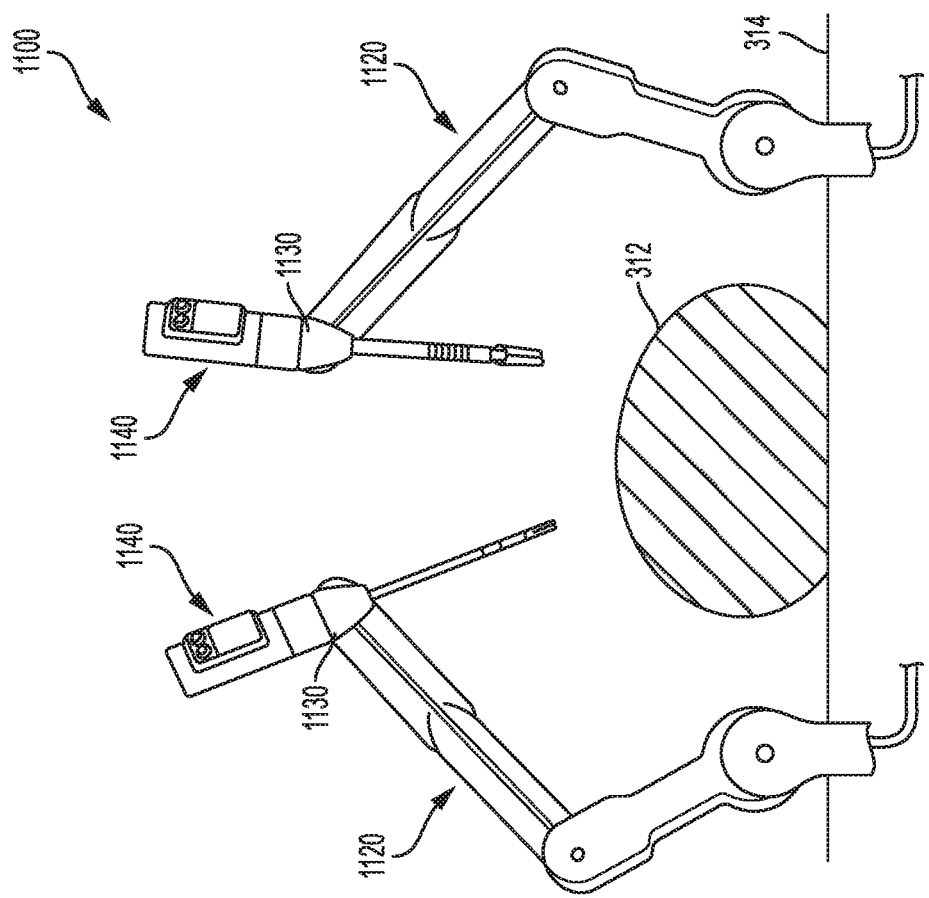

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, various surgical methods, devices, and systems are provided that for facilitating attachment/detachment between an electrosurgical robotic arm and a trocar that is configured to receive a tool coupled to the electrosurgical robotic arm. Often during a robotic surgical procedure it is necessary to remove a tool from a trocar disposed in a patient for the purposes of reloading the tool or swapping out the tool for another tool. Current procedures require this to be done manually, requiring a user to enter into the sterile field in order to remove and/or reload the tool. Accordingly, various methods and devices are provided that allow tool reload or exchange to be done automatically, preferably without the aid of a user. This can be achieved by providing a robotic arm having a trocar holding member that is configured with any one or more of the following capabilities: (1) sensing a location of a trocar positioned within a patient, (2) acquiring/engaging the trocar, and (3) orienting the trocar into a desired predetermined orientation.

Sensing can be achieved using a variety of techniques. For example, in one embodiment the trocar holding member can include one or more sensors disposed thereon and configured to sense a location of a trocar. The trocar can have corresponding sensors for allowing the trocar holding member to sense the trocar. The sensors can also, in certain embodiments, be configured to indicate an orientation of the trocar. In other aspects, the trocar can have sensors and it can be configured to sense its position within a three-dimensional space and to communicate that sensed position directly to the robotic system, thus allowing the robotic system to manipulate the trocar holding member into proximity with the trocar using the known trocar location. In other aspects, a user can simply view the position of the trocar on the display showing an image of the surgical site, as obtained from an endoscopic camera.

Acquiring or engaging the trocar can also be achieved using a variety of techniques. In one embodiment, the trocar holding member can include one or more grasping arms that are movable between open and closed positions for grasping a trocar. In other embodiments, the trocar holding member can be C-shaped or ring shaped and it can be configured to be placed around or to automatically receive the trocar therein. In certain aspects, the trocar holding member can include one or more magnets configured to attract a ferromagnetic material on the trocar. Such a configuration can allow the trocar holding member to automatically pull the trocar into the trocar holding member when positioned in proximity with one another. The magnets can optionally be configured to engage the trocar in a predetermined orientation, thus orienting the trocar relative to the trocar holding member.

Methods and devices for orienting a trocar relative to a trocar are also provided. It can be particularly important to orient the trocar relative to the trocar holding member so as to prevent an insufflation port, such as a stop-cock, on the trocar from being inadvertently pressed into a tissue surface. By knowing the orientation, the trocar holding member and trocar can be manipulated without causing any harm to the patient. Proper orientation can be achieved using a number of techniques. For example, as indicated above one or more magnets on the trocar holding member can be configured to engage the trocar in a predetermined orientation. This can be achieved, for example, by providing corresponding magnets on the trocar that only mate in one orientation. In other embodiments, the trocar holding member can include one or more rotating wheels that are configured to rotate the trocar into a predetermined orientation. The trocar and/or trocar holding member can also include an indicator for indicating proper orientation, and/or a locking mechanism for maintain the trocar in the proper orientation. For example, the trocar can include engagement features that engage with the trocar holding member when the trocar is in the proper orientation. In other aspects, the trocar holding member can include one or more cams configured to engage and lock the trocar into a fixed orientation.

A person skilled in the art will appreciate that each of the steps of sensing, acquiring, and orienting can be performed individually, simultaneously, and in any order and in any combination. For example, a trocar holding member may be configured to orient a trocar into a predetermined orientation, either before or after engagement. In such a system, the position of the trocar may not need to be sensed. The trocar could be configured to provide this information directly to the robotic system, thereby allowing the robotic system to manipulate the trocar holding member to cause it to be positioned in engagement with the trocar. Alternatively, a user could view a position of the trocar and can manipulate the trocar holding member to cause it to be positioned in engagement with the trocar.

As indicated above, the systems, devices, and methods disclosed herein can be implemented using a robotic surgical system. FIG. 1 is a perspective view of one embodiment of a surgical robotic system that includes a patient-side portion 1100 that is positioned adjacent to a patient 312, and a user-side portion 311 that is located a distance from the patient, either in the same room and/or in a remote location. The patient-side portion 1100 generally includes one or more robotic arms 1120 having a tool driver 1130 disposed on a distal end thereof, and one or more tool assemblies 1140 that are configured to releasably couple to the tool driver 1130 of the robotic arm 1120. The user-side portion 311 generally includes a vision system 313 for viewing the patient 312 and/or surgical site, and a control system 315 for controlling the movement of the robotic arms 1120 and each tool assembly 1140 during a surgical procedure.

As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

The control system 315 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 315 can include components that enable a user to view a surgical site of a patient 312 being operated on by the patient-side portion 1100 and/or to control one or more parts of the patient-side portion 1100 (e.g., to perform a surgical procedure at the surgical site 312). In some embodiments, the control system 315 can also include one or more manually-operated input devices, such as a joystick, exoskeletal glove, a powered and gravity-compensated manipulator, or the like. These input devices can control teleoperated motors which, in turn, control the movement of the surgical system, including the robotic arms 1120 and tool assemblies 1140.

The patient-side portion can also have a variety of configurations. As depicted in FIG. 1, the patient-side portion 1100 can couple to an operating table 314. However, in some embodiments, the patient-side portion 1100 can be mounted to a wall, to the ceiling, to the floor, or to other operating room equipment. Further, while the patient-side portion 1100 is shown as including two robotic arms 1120, more or fewer robotic arms 1120 may be included. Furthermore, the patient-side portion 1100 can include separate robotic arms 1120 mounted in various positions, such as relative to the surgical table 314 (as shown in FIG. 1). Alternatively, the patient-side portion 1100 can include a single assembly that includes one or more robotic arms 1120 extending therefrom.

Figure 2:
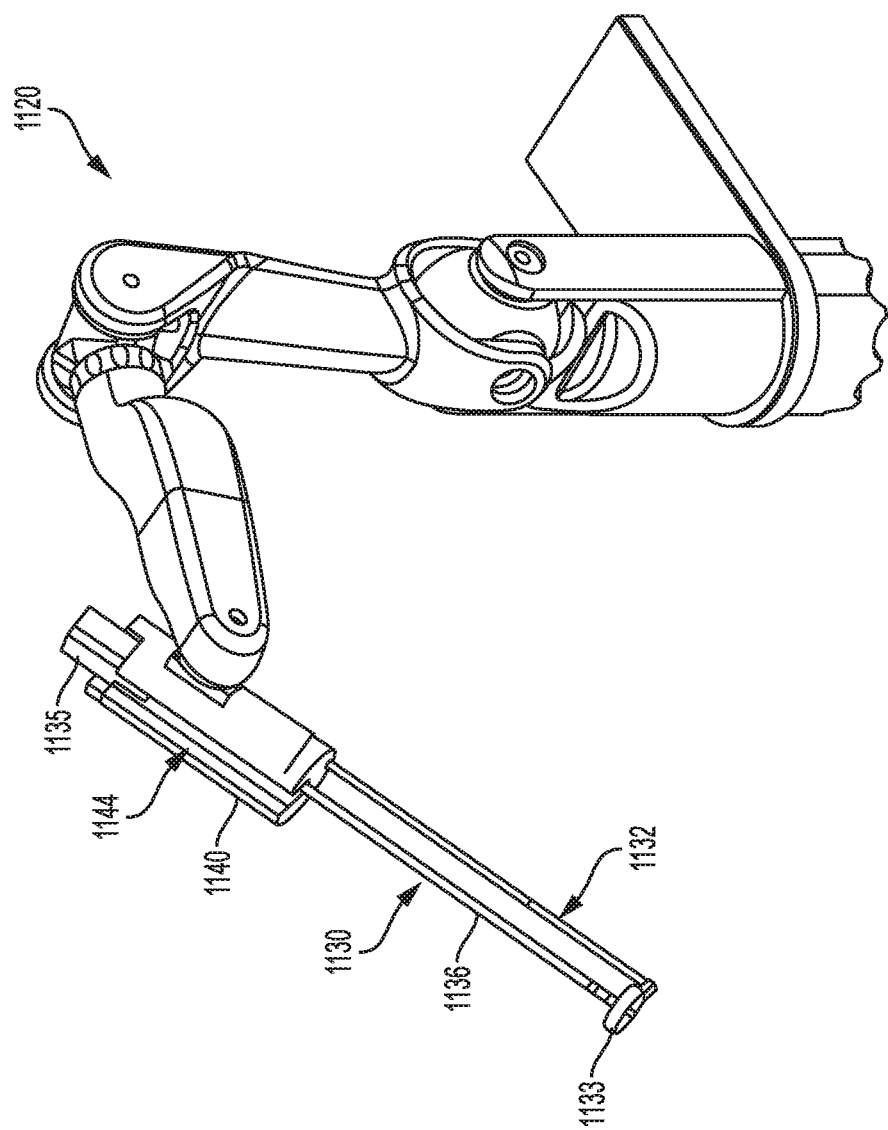
FIG. 2 is a perspective view of an embodiment of a robotic arm of a surgical robotic system with a tool assembly releasably coupled to a tool driver on the robotic arm.

FIG. 2 illustrates the robotic arm 1120 and tool assembly 1130 releasably coupled to the robotic arm 1120. The robotic arm 1120 can support and move the associated tool assembly 1130 along one or more mechanical degrees of freedom (e.g., all six Cartesian degrees of freedom, five or fewer Cartesian degrees of freedom, etc.).

The tool driver 1140 located at a distal end of the robotic arm 1120 can assist with controlling features associated with the tool assembly 1130. The robotic arm 1120 can also include a movable tool guide 1132 that can retract and extend relative to the driver 1140. A shaft of the tool assembly 1130 can extend parallel to a threaded shaft of the movable tool guide 1132 and can extend through a distal end feature, e.g., a trocar holding member 1133, of the movable tool guide 1130 and into a patient. The trocar holding member 1133 can be configured to mate with a trocar (not shown), thereby allowing the tool shaft 1136 to be advanced through the trocar and into a patient's body.

Typically, cannulas such as trocars are used to provide a pathway through a tissue surface and/or to prevent a surgical instrument or guide tube from rubbing on patient tissue. Cannulas can be used for both incisions and natural orifices. Some surgical procedures require insufflation, and the cannula can include one or more seals to prevent excess insufflation gas leakage past the instrument or guide tube. In some embodiments, the cannula can have a housing coupled thereto with two or more sealed ports for receiving various types of instruments besides the slave assembly. As will be appreciated by a person skilled in the art, any cannula known in the art can be used with the methods and devices disclosed herein.

In order to provide a sterile operation area while using the surgical system, a barrier (not shown) can be placed between the actuating portion of the surgical system (e.g., the robotic arm 1120) and the surgical instruments (e.g., the tool assembly 1130) in the sterile surgical field. A sterile component, such as an instrument sterile adapter (ISA), can also be placed at the connecting interface between the tool assembly 1130 and the robotic arm 1120. The placement of an ISA between the tool assembly 1130 and the robotic arm 1120 can ensure a sterile coupling point for the tool assembly 1130 and the robotic arm 1120. This permits removal of tool assemblies 1130 from the robotic arm 1120 to exchange with other tool assemblies 1130 during the course of a surgery without compromising the sterile surgical field.

In use, the tool assembly 1130 can be loaded from a top side of the driver 1140 with the shaft of the tool assembly 1130 being positioned in a shaft-receiving channel 1144 formed along the side of the driver 1140. In other embodiments, the shaft can extend through on opening in the tool driver 1140, or the two components can mate in various other configurations. The shaft-receiving channel 1144 allows the shaft, which extends along a central axis of the tool assembly 1130, to extend along a central axis of the driver 1140 when the tool assembly 1130 is coupled to the driver 1140. Actuation of the movable tool guide 1132 will cause the shaft 1136 to move distally into a trocar (not shown) engaged by the trocar holding member 1133.

The tool housing 1135 can include coupling features that assist with releasably coupling the tool housing 1135 to the tool driver 1140 of the robotic arm 1120. The tool housing 1135 can include driving members (e.g., gears, cables, and/or drivers) that can be directly or indirectly actuated by the one or more motors. The driving members in the tool housing 1135 can control the operation of various features associated with the end effector 1138 (e.g., clamping, firing, rotation, articulation, etc.), as well as control the movement of the shaft 1136 (e.g., rotation and/or articulation of the shaft).

The shaft 1136 can be fixed to the tool housing 1135, or it can be releasably coupled to the tool housing 1135 such that the shaft 1136 can be interchangeable with other shafts. This can allow a single tool housing 1135 to be adaptable to various shafts 1136 having different end effectors 1138. The shaft 1136 can include actuators and connectors that extend along the shaft and assist with controlling the actuation and/or movement of the end effector 1138 and/or shaft 1136. The shaft 1136 can also include one or more joints or wrists 1137 that allow a part of the shaft 1136 or the end effector 1138 to rotate and/or articulate relative to the longitudinal axis of the shaft 1136. This can allow for fine movements and various angulation of the end effector 1138 relative to the longitudinal axis of the shaft 1136. The end effector 1138 can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

Figure 3C:
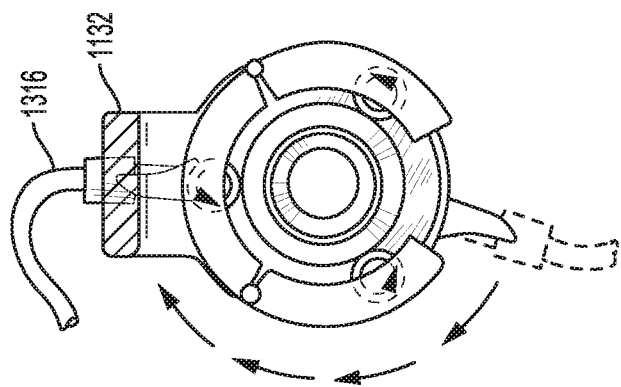
FIG. 3C is a top view of the trocar holding member of FIG. 3A, showing the trocar oriented relative to the trocar holding member.
Figure 3B:
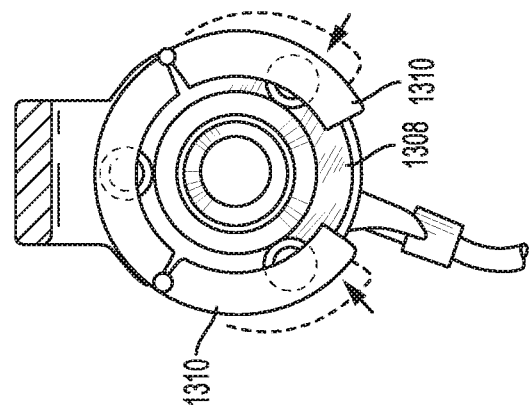
FIG. 3B is a top view of the trocar holding member of FIG. 3A, showing the pivoting arms in the closed position engaging a trocar.
Figure 3A:
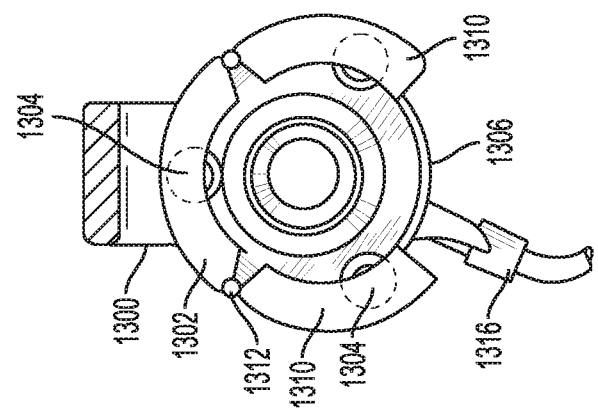
FIG. 3A is a top view of one embodiment of a trocar holding member having pivoting arms shown in an open position.

As indicated above, in an exemplary embodiment the trocar holding member 1133 is configured with any one or more of the following capabilities: (1) sensing a location of a trocar positioned within a patient, (2) acquiring/engaging the trocar, and (3) orienting the trocar into a desired predetermined orientation. FIGS. 3A-3C illustrate one exemplary embodiment of a trocar holding member 1300 having a plurality of electromagnetic trocar engagement portions 1302. The electromagnetic trocar engagement portion 1302 of the trocar holding member 1300 can include an electromagnet (illustrated in FIGS. 4A and 4B) and one or more wheels 1304. In some use cases, the trocar holding member 1300 can be positioned proximate to a trocar 1306. The trocar 1306 can include a ferrous ring 1308 (illustrated in FIG. 4A) and the electromagnets can be activated to generate an electromagnetic field attracting the ferrous ring 1308 of the trocar 1306 into the trocar holding member 1300.

One or more of the trocar engagement portions 1302 can be a pivoting arm 1310 that attaches to the trocar holding member 1300 at a pivot 1312. The illustrated embodiment has two pivoting arms 1310 positioned on opposite sides of the trocar holding member. The pivoting arm 1310 can be configured to pivot inward to securely engage the trocar 1306 within the trocar holing member 1300.

As illustrated in FIG. 3B, when the pivoting arms 1310 are closed, the one or more wheels 1304 can be configured to engage with a neck 1314 (FIG. 4A) of the trocar 1306 to prevent lateral movement of the trocar 1306 with respect to the trocar holding member 1300.

The trocar holding member 1300 can be configured to orient the trocar 1306 to mate the trocar to the trocar holding member 1300 in a desired orientation. A desired orientation may be positioning a stopcock 1316 of the trocar 1306 such that the stopcock does not extend toward or into the tissue of the patient. For example, a desired orientation of the trocar 1306 can include positioning the stopcock 1316 to be aligned with the main body of the trocar holding member 1300, i.e., on a side opposite to the opening between the pivoting arms 1310, as shown in FIG. 3C.

In one example, the trocar holding member 1300 can be configured to orient the trocar 1306 by rotating one or more of the wheels 1304. A wheel 1304 can have an associated motor which rotates the wheel 1304 which, in turn, causes the trocar 1306 to rotate within the trocar holing member

1300. In another example, a wheel 1304 can be include one or more magnetic or ferrous elements allowing the wheel 1304 to be rotated based on an electrical current applied in the vicinity of the wheel 1304. In yet another example, an electrical current may be applied to the trocar engagement portions 1302 of the trocar holding member 1300, the electrical current generating an electromagnetic field in the vicinity of the trocar engagement portions 1302 that affects a ferrous ring 1308 on the trocar 1306. The electrical current can be applied in a way such as to rotate the electromagnetic field in a clockwise or anti-clockwise direction around the trocar holding member 1300 and in turn rotating the trocar 1306. In some variations, the wheels 1304 may have magnetic properties.

Figure 4B:
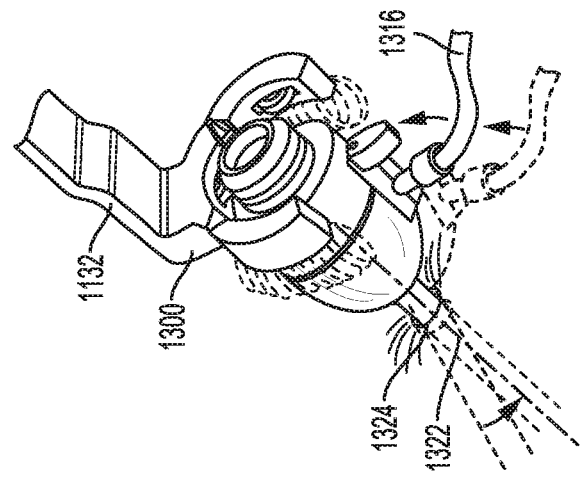
FIG. 4B is a perspective view of the trocar holding member of FIG. 4B about to engage the trocar of FIG. 4B.
Figure 4A:
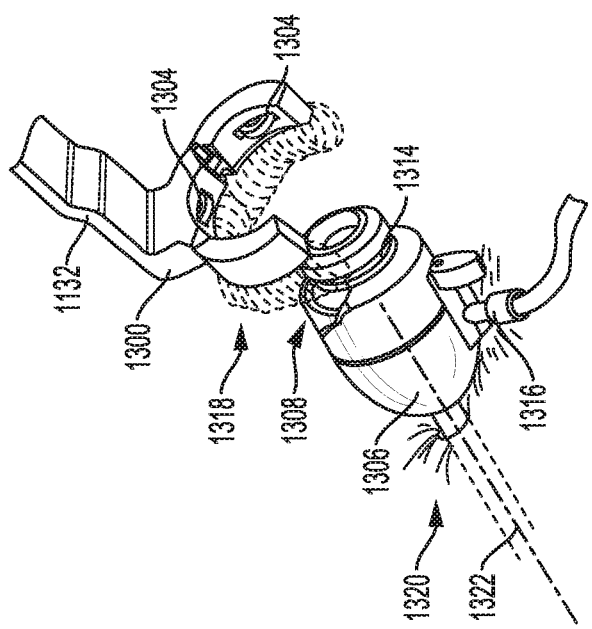
FIG. 4A is a perspective view of the trocar holding member of FIG. 3C positioned in proximity to a trocar disposed through a tissue surface.

As shown in FIGS. 4A-4B, the main frame or body of the trocar holding member 1300 includes a first wheel 1304 disposed on an inner surface thereof, and each pivoting arm 1310 also includes a wheel 1304 disposed on an inner surface thereof. The three wheels 1304 can function together to rotate the trocar when the trocar is engaged within the trocar holding member 1300.

In use the trocar holding member 1300 can be positioned in the vicinity of a trocar 1306, as illustrated in FIG. 4A. The trocar holding member 1300 can include one or more electromagnetic elements 1318, referred to herein as an electromagnet. An electrical current can be applied to the electromagnet 1318 of the trocar holding member 1300 causing an electromagnetic field to be generated in the vicinity of the electromagnet 1318. This can, in turn, attract the ferrous ring 1308 of the trocar 1306, and therefore the trocar 1306, toward the electromagnet 1318, as illustrated in FIG. 4B. At this point, one or more of the trocar engagement portions 1302 can still be in an open position.

The attraction of the trocar 1306 into the trocar holding member 1300 can cause the trocar 1306 to pivot with respect to the patient 1320. In FIG. 4A, the trocar 1306 is shown lying on the tissue of the patient 1320. When the trocar 1306 is magnetically pulled into the trocar holding member 1300, the trocar 1306 is lifted off of the tissue of the patient 1320, as illustrated in FIG. 4B. This can have the effect of causing the cannula 1322 of the trocar 1306 to be orientated to a position that provides an improved seal with the patient at the entry point 1324 into the patient 1320. Similarly, the stopcock 1316 can be lifted off of the tissue of the patient 1320.

In one embodiment, the electromagnet 1318 may be a permanent magnet. When the trocar holding member 1300 is moved within proximity of a trocar 1306, the permanent magnet can be configured to automatically attract the trocar into the trocar holding member 1300. In another embodiment, the trocar holding member 1300 can include one or more sensors, such as hall effect sensors, that can detect the presence of the ferrous ring 1308 of the trocar 1306. The hall effect sensors can generate a signal that causes the electromagnet 1318 to be activated, attracting the trocar 1306 into the trocar holding member 1300.

Subsequent to the trocar 1306 engaging with the trocar holding member 1300, one or more trocar engagement portions 1302 may pivot closing around the trocar 1306 holding the trocar in place. The trocar 1306 can be rotated within the trocar holding member 1300 to position the trocar 1306 at a desired orientation.

FIGS. 5A-5C illustrate the trocar 1306 positioned on its side along the tissue surface, and the trocar holding member 1300 is positioned to engage with the trocar 1306. The trocar 1306 can be resting on the tissue of the patient 1320 hampering the ability of the trocar to be oriented at a desired location for performing surgical functions. Furthermore, a trocar 1306 lying on the tissue surface as shown can present a suboptimal seal at the entry point 1324 into the patient 1320. The trocar holding member 1300 can be brought toward the trocar 1306 and brought within the vicinity of the trocar 1306. Prior to an attempt to engage with the trocar 1306, the trocar holding member 1300 can be brought within a threshold distance of the trocar 1306. The trocar holding member 1300 can also be brought within a threshold angle of the trocar 1306. A threshold angle can be determined based on the relative positions of a trocar central axis 1326 and a trocar holding member central axis 1328. When the angle 1330 between the trocar central axis 1326 and the trocar holding member central axis 1328 is within a threshold range, the electromagnet 1318 of the trocar holding member 1300 (illustrated in FIGS. 4A and 4B) can be activated attracting the trocar 1306 into the trocar holding member 1300.

As illustrated in FIG. 5B, after the trocar 1306 has magnetically attached to the trocar holding member 1300, the trocar holding member 1300 can move the trocar 1306 to a desired angle relative to the trocar holding member 1300. The desired angle can be an angle between the trocar central axis 1326 and the trocar holding member central axis 1328 at which one or more robotic instruments can be introduced into the trocar 1306 and through the cannula 1322.

Referring to FIG. 5C, once the trocar central axis 1326 and the trocar holding member central axis 1328 are within an acceptable angle of one another, the trocar holding member 1300 can be configured to cause the trocar engagement portion 1302 to engage with the trocar 1306. The engagement of the trocar engagement portion 1302 with the trocar 1306 can cause the trocar central axis 1326 to align with the trocar holding member central axis 1328. Simultaneously with or subsequent to the trocar 1306 being secured into the trocar holding member 1300, the trocar holding member 1300 can be configured to cause the trocar 1306 to rotate to a desired position.

Figure 6B:
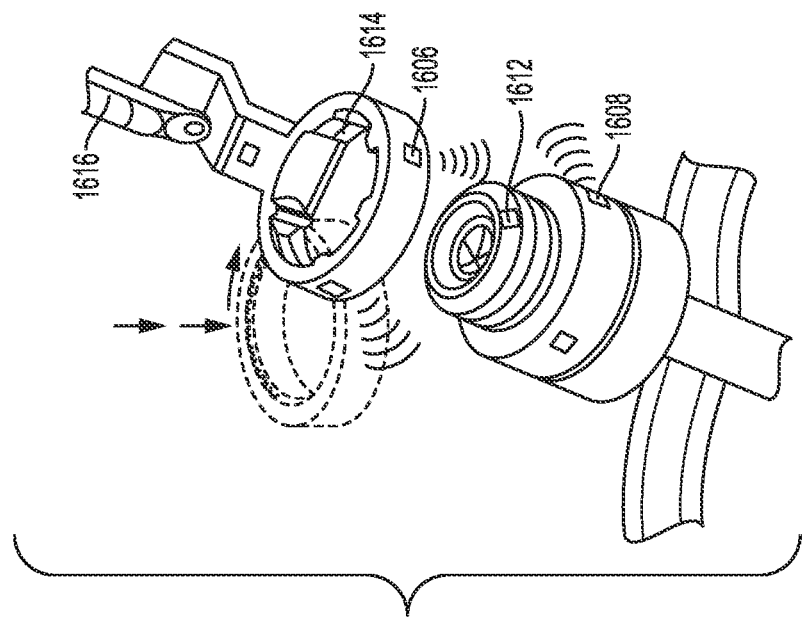
FIG. 6B is a perspective view of the trocar holding member and trocar of FIG. 6A aligned for mating.
Figure 6A:
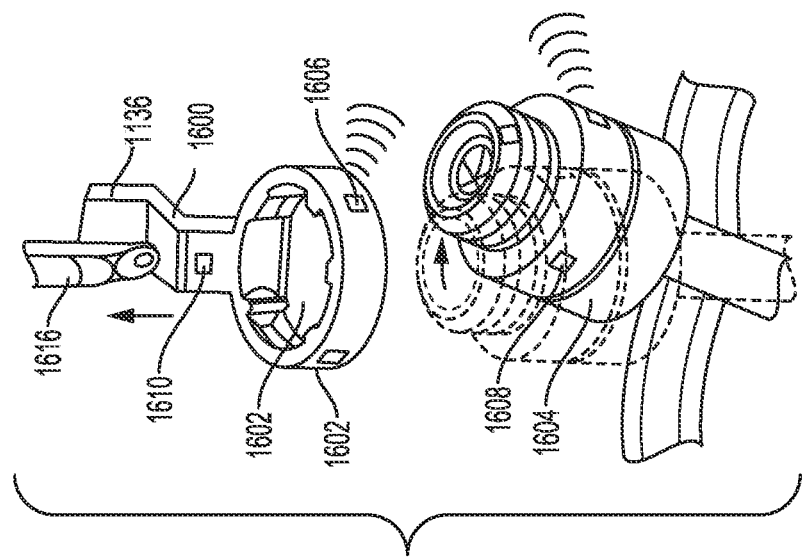
FIG. 6A is a perspective view of another embodiment of a trocar holding member positioned in proximity to a trocar.

FIGS. 6A and 6B illustrate another embodiment of a trocar holding member 1600 having a trocar holding ring 1602 for engaging with a trocar 1604. The trocar holding member 1600 can be disposed at the end of a tool shaft 1136. FIG. 6A illustrates the trocar holding member 1600 positioned a distance apart from the trocar 1604. The trocar holding member 1600 may be disengaged from the trocar 1604 for any number of reasons, including for replacing a tool cartridge, adjustments, or the like. FIG. 6B illustrates the trocar holding member 1600 being moved into proximity with the trocar 1604.

The trocar holding member 1600 and the trocar 1604 can include one or more sensors, for example, hall sensors, to detect the relative positions of the trocar holding member 1600 and the trocar 1604. Ring sensors 1606 may be disposed on the trocar holding ring 1602 of the trocar holding member 1600. Trocar sensors 1608 may be disposed on the trocar 1604. The ring sensors 1606 can be configured to detect the presence of the trocar sensors 1608. Each of the trocar sensors 1608 may have a different signal facilitating a determination of the relative position of each trocar sensor 1608 with respect to the ring sensors 1606. The robotic system controlling the tool shaft 1136 can be configured to position and orient the trocar holding ring 1602 based on the signals received from the trocar sensors 1608. As illustrated in FIG. 6B the trocar holding ring 1602 is positioned such that a central axis of the trocar holding ring 1602 and a central axis of the trocar 1604 are aligned.

The trocar holding member 1600 can include a depth sensor 1610 on the tool shaft 1136. A complimentary depth sensor 1612 can be disposed on the trocar 1604. The depth sensors 1610 and 1612 can be configured to facilitate a determination of the how far the trocar 1604 has extended through the trocar holding ring 1602. When the trocar 1604 and the trocar holding ring 1602 are at an attachment position, trocar engagers 1614 can be activated to secure the trocar 1604 into the trocar holding ring 1602.

After the trocar 1604 is in a secure engagement with the trocar holding ring 1602, the robotic control system can be configured to extend an instrument 1616 into and through the trocar 1604.

In one exemplary variation, the ring sensors 1606 and the trocar sensors 1608 can be Hall effect sensors. The illustrated sensors are spaced around an external perimeter of the trocar holding ring 1602, however they can be positioned at various locations.

Figure 7C:
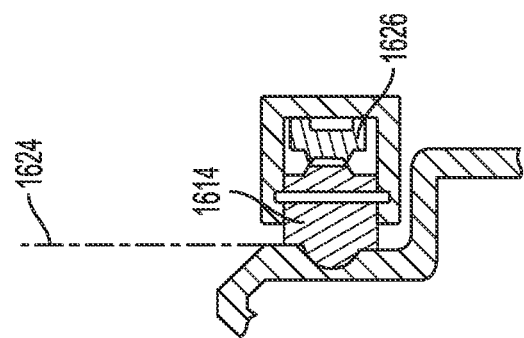
FIG. 7C illustrates the trocar engaging feature of FIG. 7B with the trocar and trocar holding member in a mated configuration.
Figure 7B:
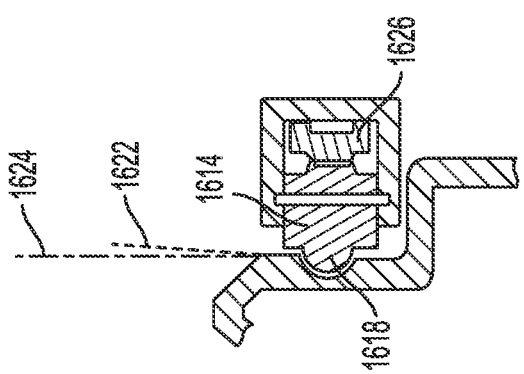
FIG. 7B illustrates the trocar engaging feature of FIG. 7A with the trocar engaging feature shown in an extend position.
Figure 7A:
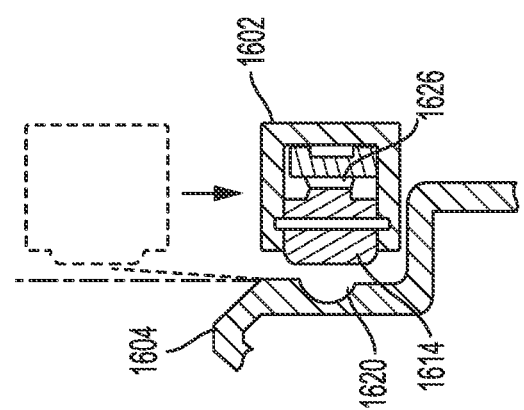
FIG. 7A illustrates one embodiment of a trocar engaging feature formed between a trocar holding member and a trocar, with the trocar engaging feature shown in a retracted position.

FIGS. 7A-7C illustrate trocar engaging features formed on an internal surface of the trocar holding ring 1602 and configured to engage the trocar 1604. In this embodiment, each trocar engager 1614 is in the form of a closure cam that is movable between a retracted position, in which the closure cam is retracted within the trocar holding ring 1602, and an extended position, in which the closure cam is extended from the trocar holding ring 1602. The closure cam can have a bulge or protrusion 1618 formed thereon. The bulge 1618 can fit into a complimentary trocar recess 1620 formed in the trocar 1604.

FIG. 7A illustrates the trocar holding ring 1602 being positioned in close proximity with the trocar 1604. The trocar engagers 1614 are shown in the retracted position. When the trocar holding ring 1602 is at a desired position and angle with respect to the trocar 1604, the trocar engagers 1614 can moved to an extended. A determination of the position of the trocar holding ring 1602 and the trocar 1604 can be based on signals received from one or more sensors disposed on the trocar 1604, the trocar holding ring 1602, and/or the tool shaft 1136.

FIG. 7B illustrates the trocar holding ring 1602 positioned in close proximity to the trocar 1604. The trocar engagers 1614 are extended. In one embodiment, the trocar engager 1614 can be extended by a gear 1626 configured to rotate causing the trocar engager 1614 to extend.

FIG. 7C illustrates the trocar engager 1614 engaged with the recess in the trocar 1604. As the trocar engager 1614 engages with the trocar 1604, the axis 1622 of the trocar 1604 is brought into alignment with the axis 1624 of the trocar holding ring 1602.

Figure 8:
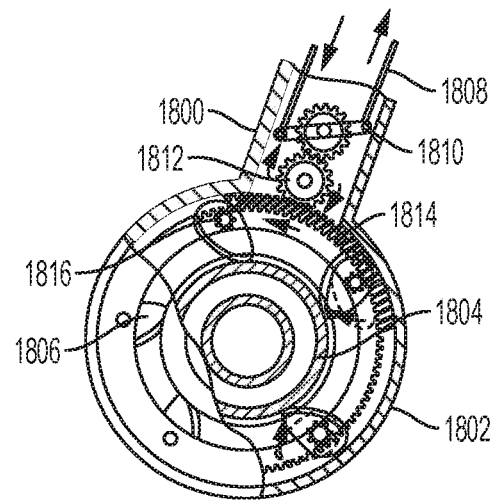
FIG. 8 is a top view of one embodiment of a gear assembly for actuating a trocar engaging feature.

FIG. 8 illustrates one exemplary embodiment of a trocar engagement member 1800 having a trocar holding ring 1802 engaged with a trocar 1804. The trocar 1804 can be secured into the trocar holding ring 1802 by a plurality of engagement portions 1814. The engagement portions 1814 can be in the form of closure cams. FIG. 8 shows a mechanically controlled trocar engagement system. The robotic computer system can be configured to actuate a motor that is connected to a cable 1808. In one exemplary embodiment, the motor that controls cable 1808 is disposed within a tool driver disposed on the distal end of a robotic arm and that couples to a housing of the tool having the tool shaft 1136 extending therefrom. The cable 1808 can be attached to a pulley 1810. The pulley 1810 can be attached to one or more gears 1812. Extension or retraction of the cable 1808 can cause the one or more gears 1812 to rotate. The gear(s) 1812 can, in turn, can rotate a ring gear 1814. The ring gear 1814 can be a gear with teeth facing internally into the central cavity of the trocar holding ring 1802.

A trocar engager gear 1816 can be attached to each trocar engager 1806. The trocar engager gear 1816 can engage with the ring gear 1814 which can cause the trocar engager gear 1816 to rotate each trocar engager 1806 to engage with the trocar 1804. Thus, the trocar 1804 can be securely engaged with the trocar holding ring 1802.

Figure 9:
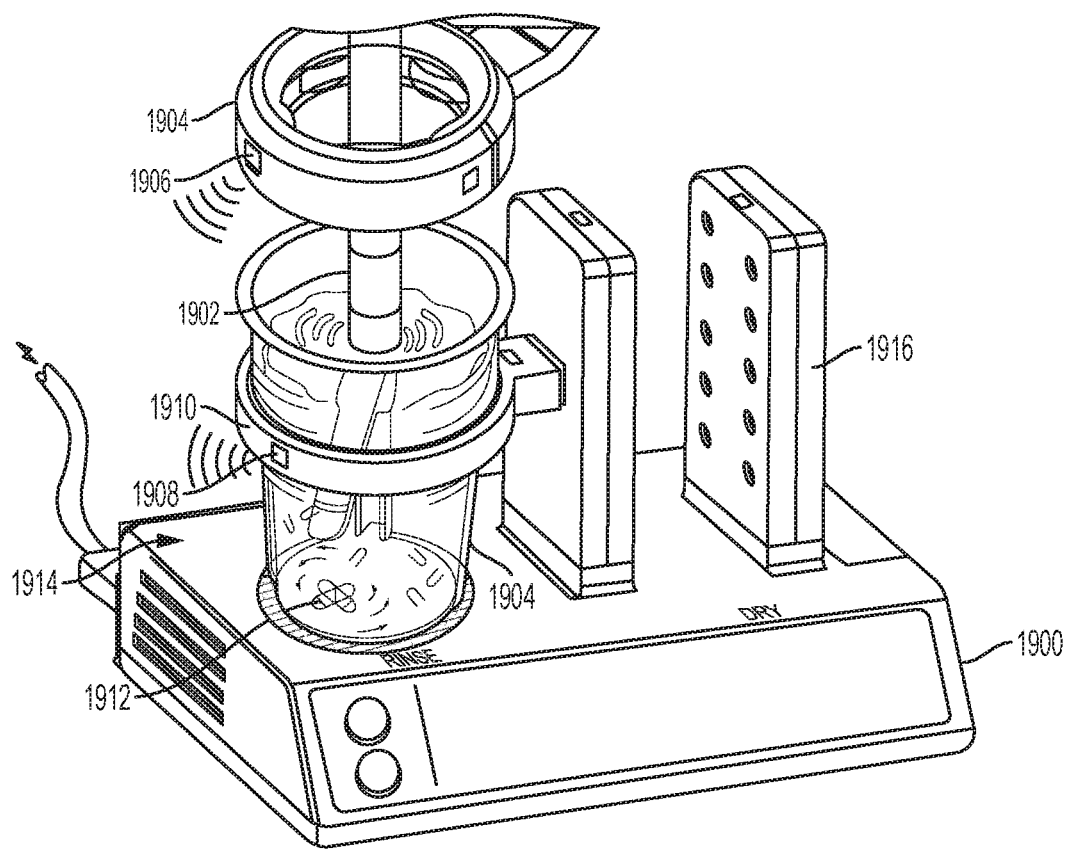
FIG. 9 is a perspective view of one embodiment of a cleaning and drying station, showing an end effector disposed within the cleaning station.

FIG. 9 illustrates one embodiment of an automated cleaning station 1900. The automated cleaning station 1900 can be configured to automatically clean surgical tools 1902. Another cleaning station is described in U.S. Pat. No. 8,931,682 titled "Robotically-Controlled Shaft Based Rotary Drive Systems for Surgical Instruments" which issued on Jan. 13, 2015, the disclosure of which is incorporated herein in its entirety.

The cleaning station 1900 can include a vessel 1904. The vessel 1904 can be filled with a saline solution for cleaning the surgical tool 1902. The vessel 1904 can be disposable. In some exemplary embodiments, the surgical tool 1902 may be an end effector and the cleaning station 1900 can be configured to clean staples off of the end effector 1902.

The robotic system can be configured to move the surgical tool 1902 disposed at a robotic arm, such as robotic arm 1120 illustrated in FIG. 2, to the cleaning station 1900. The tool shaft of the robotic arm can include a trocar engagement member 1904 having one or more sensors 1906. The cleaning station 1900 may include one or more sensors 1908 in proximity to the vessel 1904. In one embodiment the sensors 1908 may be disposed on a holder 1910 configured to secure the vessel 1904 to the cleaning station 1900.

The sensors 1906 disposed on the trocar engagement member 1904 can be configured to detect the presence of the sensors 1908 disposed on the cleaning station 1900, and vice versa. Based on signals received from various ones of the sensors 1906 and/or sensors 1908, a determination can be made as to the relative position of the trocar engagement member 1904 and the cleaning station 1908. In turn, the relative position of the surgical tool 1902 can be determined relative to the base and sides of the vessel 1904.

The robotic system can be configured to lower the surgical tool 1902 into the vessel 1904. A stirrer 1912 can be disposed in the bottom of the vessel 1904 and it can be configured to rotate to thereby agitate the liquid within the vessel 1904 facilitating cleaning of the surgical tool 1902. The stirrer 1912 can be rotated using magnets disposed in the base 1914 of the cleaning station 1900. The base 1914 can include one or more surface sensors. The surface sensors can be configured to detect the amount of liquid in the vessel 1904. As the cleaning station 1900 cleans the surgical tool 1902, debris can be removed from the surgical tool 1902. The debris, for example staples, can collect in the vessel 1904 increasing the weight of the vessel 1904 and reducing the weight of the surgical tool 1902. The surgical tool 1902 can have a known weight. The robotic system can be configured to detect the weight of the debris on the surgical tool 1902. When the weight of the vessel 1904 increases by the determined weight of the debris, the robotic system can be configured to stop cleaning the surgical tool 1902 and move it to a drying station 1916.

Figure 10:
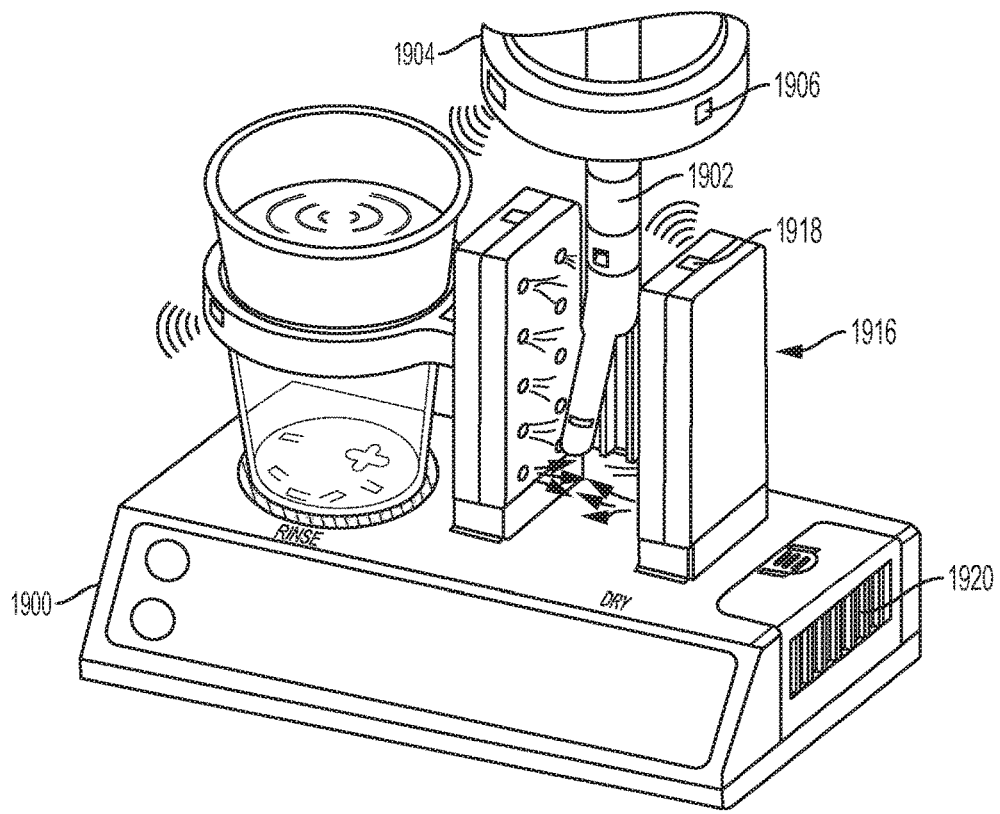
FIG. 10 is a perspective view of the cleaning and drying station of FIG. 9, showing the end effector disposed within the drying station.

FIG. 10 illustrates the automated cleaning station 1900, wherein the surgical tool 1902 has been moved to the drying station 1916. The drying station 1916 can include one or more sensors 1918. The sensors 1918 can be configured to emit a signal. The sensor(s) 1906 disposed on the trocar holding ring 1904 can be configured to detect the signals emitted by the sensors 1918, and vice versa. A determination of the position of the trocar holding ring 1904, and therefore the surgical tool 1902, relative to the drying station 1916 can be made. The robotic system can be configured to automatically position the surgical tool within the drying station 1916 for drying by the drying station 1916. One or more fans and/or heaters can be disposed within the drying station 1916. Air can be blown from the drying station 1916 onto the surgical tool 1902 drying the surgical tool 1902. Air can be received by the drying station 1916 through an air intake 1922.

Figure 11A:
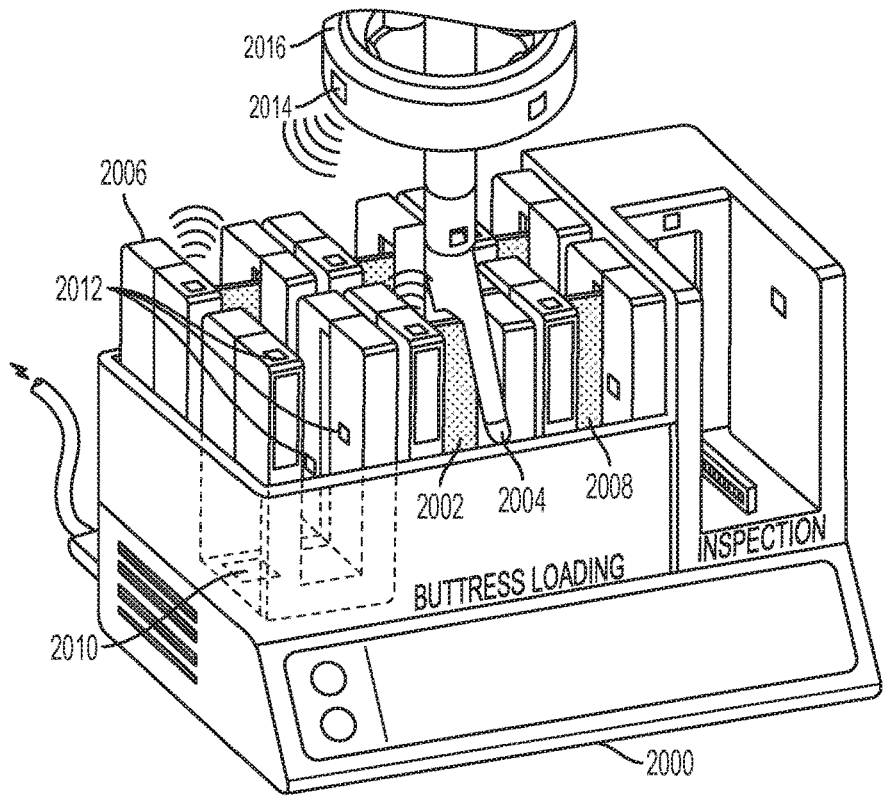
FIG. 11A is a perspective view of one embodiment of a cartridge loading and inspection station, showing an end effector engaging a cartridge.
Figure 11B:
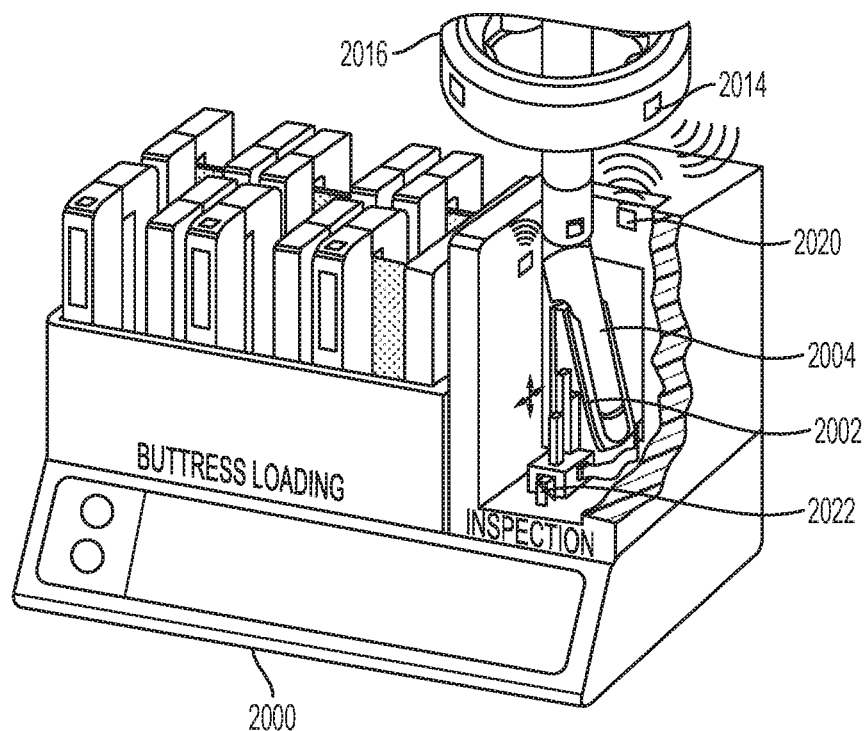
FIG. 11B is a perspective view of the cartridge loading and inspection station of FIG. 11A, showing the end effector at the inspection station.

FIGS. 11A and 11B illustrate a buttress reloading and inspection station 2000. A buttress reloading and inspection station 2000 can be configured to facilitate the automatic reloading of a buttress 2002 onto an end effector 2004. The buttress reloading and inspection station 2000 can be configured to house one or more cartridges 2006. The cartridges 2006 can be configured to hold buttress sheets 2008 of buttresses 2002. The buttress cartridges 2006 can be configured to communicate with the buttress reloading and inspection station 2000 through a buttress cartridge connector 2010.

The cartridges 2006 can include at least one cartridge sensor 2012. In the exemplary embodiment illustrated in FIG. 11A, each buttress cartridge 2006 includes three Hall effect sensors. The buttress cartridge sensors 2012 can be configured to wirelessly communicate with trocar engagement member sensors 2014 disposed on a trocar engagement member 2016. The cartridge sensor(s) 2012 and the trocar engagement member sensors 2014 can be configured facilitate determination the position of the trocar engagement member 2016, and therefore the end effector 2004, relative to the buttress cartridge 2006.

The end effector 2004 can be positioned with the aid of the sensors 2012 and the sensors 2014 within a buttress cartridge 2006 for installation of a buttress 2002 onto the end effector 2004.

FIG. 11B illustrates an embodiment of an end effector 2004 having a newly installed buttress 2002 being inspected at an inspection station 2018 of a buttress reloading and inspection station 2000. The inspection station 2018 can include at least one inspection station sensor 2020 configured to communicate with the trocar engagement member sensors 2014 of the trocar engagement member 2016. The robotic control system can be configured to position the trocar engagement member 2016 and therefore the end effector within the inspection station 2018 without hitting the sides of the inspection station 2018.

The inspection station 2018 can include at least one inspection sensor 2022. The inspection sensor(s) 2022 can be configured to inspect the end effector 2004. The inspection sensor(s) 2022 can have one or more degrees of freedom allowing the sensors to move around to inspect the end effector 2004. In the embodiment illustrated in FIG. 11B, the inspection sensor(s) 2022 is a camera. The camera can be disposed on a sliding platform allowing the camera to inspect the end effector 2004 from multiple positions. The camera can be configured to slide laterally as well as be elevated to inspect the end effector 2004. The camera may be looking for exposed anvil pockets or exposed staple pockets.

The systems, devices, and methods disclosed herein can be implemented using one or more computer systems, which may also be referred to herein as digital data processing systems and programmable systems.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system may include clients and servers. A client and server are generally remote from each other and typically interact through a communication network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, e.g., a mouse, a trackball, etc., by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 12:
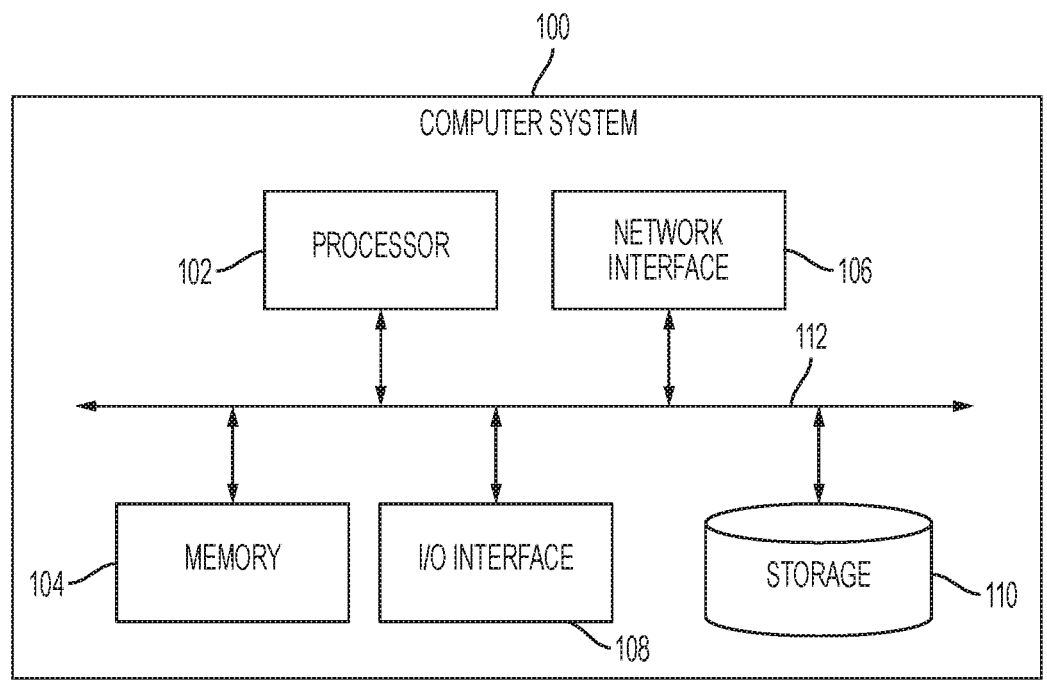
FIG. 12 illustrates one exemplary embodiment of a computer system having one or more features consistent with the present description.

FIG. 12 illustrates one exemplary embodiment of a computer system 100. As shown, the computer system 100 includes one or more processors 102 which can control the operation of the computer system 100. "Processors" are also referred to herein as "controllers." The processor(s) 102 can include any type of microprocessor or central processing unit (CPU), including programmable general-purpose or special-purpose microprocessors and/or any one of a variety of proprietary or commercially available single or multi-processor systems. The computer system 100 can also include one or more memories 104, which can provide temporary storage for code to be executed by the processor(s) 102 or for data acquired from one or more users, storage devices, and/or databases. The memory 104 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system 100 can be coupled to a bus system 112. The illustrated bus system 112 is an abstraction that represents any one or more separate physical busses, communication lines/interfaces, and/or multi-drop or point-to-point connections, connected by appropriate bridges, adapters, and/or controllers. The computer system 100 can also include one or more network interface(s) 106, one or more input/output (IO) interface(s) 108, and one or more storage device(s) 110.

The network interface(s) 106 can enable the computer system 100 to communicate with remote devices, e.g., other computer systems, over a network, and can be, for non-limiting example, remote desktop connection interfaces, Ethernet adapters, and/or other local area network (LAN) adapters. The IO interface(s) 108 can include one or more interface components to connect the computer system 100 with other electronic equipment. For non-limiting example, the IO interface(s) 108 can include high speed data ports, such as universal serial bus (USB) ports, 1394 ports, Wi-Fi, Bluetooth, etc. Additionally, the computer system 100 can be accessible to a human user, and thus the IO interface(s) 108 can include displays, speakers, keyboards, pointing devices, and/or various other video, audio, or alphanumeric interfaces. The storage device(s) 110 can include any conventional medium for storing data in a non-volatile and/or non-transient manner. The storage device(s) 110 can thus hold data and/or instructions in a persistent state, i.e., the value(s) are retained despite interruption of power to the computer system 100. The storage device(s) 110 can include one or more hard disk drives, flash drives, USB drives, optical drives, various media cards, diskettes, compact discs, and/or any combination thereof and can be directly connected to the computer system 100 or remotely connected thereto, such as over a network. In an exemplary embodiment, the storage device(s) can include a tangible or non-transitory computer readable medium configured to store data, e.g., a hard disk drive, a flash drive, a USB drive, an optical drive, a media card, a diskette, a compact disc, etc.

The elements illustrated in FIG. 12 can be some or all of the elements of a single physical machine. In addition, not all of the illustrated elements need to be located on or in the same physical machine. Exemplary computer systems include conventional desktop computers, workstations, minicomputers, laptop computers, tablet computers, personal digital assistants (PDAs), mobile phones, and the like.

The computer system 100 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 100 can also include a web server for generating and/or delivering the web pages to client computer systems.

In an exemplary embodiment, the computer system 100 can be provided as a single unit, e.g., as a single server, as a single tower, contained within a single housing, etc. The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

A computer system can also include any of a variety of other software and/or hardware components, including by way of non-limiting example, operating systems and database management systems. Although an exemplary computer system is depicted and described herein, it will be appreciated that this is for sake of generality and convenience. In other embodiments, the computer system may differ in architecture and operation from that shown and described here.

The terminology used herein is not intended to limit the invention. For example, spatially relative terms, e.g., "superior," "inferior," "beneath," "below," "lower," "above," "upper," "rearward," "forward," etc., may be used to describe one element's or feature's relationship to another element or feature as illustrated in the figures. These spatially relative terms are intended to encompass different positions and orientations of the device in use or operation in addition to the position and orientation shown in the figures. For example, if the device in the figures is turned over, elements described as "inferior to" or "below" other elements or features would then be "superior to" or "above" the other elements or features. Likewise, descriptions of movement along and around various axes include various special device positions and orientations. As will be appreciated by those skilled in the art, specification of the presence of stated features, steps, operations, elements, and/or components does not preclude the presence or addition of one or more other features, steps, operations, elements, components, and/or groups described herein. In addition, components described as coupled may be directly coupled, or they may be indirectly coupled via one or more intermediate components.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical system, comprising:
   an electromechanical robotic arm;
   a trocar holding ring disposed on a distal end of the electromechanical robotic arm and configured to mate with a trocar, the trocar holding ring having at least one engagement mechanism configured to engage and orient the trocar to mate the trocar to the trocar holding ring in a desired orientation; and
   a controller operatively coupled to the at least one engagement mechanism, the controller configured to determine a position of the trocar relative to the trocar holding ring and to cause the at least one engagement mechanism to engage the trocar when the trocar is determined by the controller to be at a predetermined position relative to the trocar holding ring.

2. The surgical system of claim 1, wherein the trocar holding ring has at least one ring sensor disposed on the trocar holding ring and configured to sense at least one of a position and an orientation of a trocar.

3. The surgical system of claim 2, wherein the at least one ring sensor is configured to detect a presence of at least one trocar sensor on a trocar.

4. The surgical system of claim 3, wherein the at least one trocar sensor comprises a plurality of trocar sensors, and each of the plurality of trocar sensors is configured to emit a distinct signal to facilitate a determination of a relative position of each of the plurality of trocar sensors with respect to the at least one ring sensor.

5. The surgical system of claim 3, wherein the controller is configured to receive data from the at least one trocar sensor relating to at least one of the position and the orientation of the trocar, and to transmit instructions to the electromechanical robotic arm to cause the electromechanical robotic arm to orient the trocar holding ring based on the received data.

6. The surgical system of claim 1, further comprising a depth sensor disposed on the trocar holding ring, the depth sensor being operably coupled to the controller and configured to facilitate a determination, by the controller, of an extent to which a portion of the trocar has extended through the trocar holding ring.

7. The surgical system of claim 1, wherein the at least one engagement mechanism comprises a closure cam movable between a retracted position, in which the closure cam is retracted within the trocar holding ring, and an extended position in which the closure cam extends from the trocar holding ring, and the engagement of the at least one engagement mechanism includes moving the closure cam between the retracted position and the extended position.

8. The surgical system of claim 1, wherein the at least one engagement mechanism is configured to fit into a complementary recess formed in the trocar.

9. A surgical system, comprising:
   an electromechanical robotic arm;
   a trocar;
   a trocar holding ring disposed on a distal end of the electromechanical robotic arm and configured to mate with the trocar, the trocar holding ring having at least one engagement mechanism configured to engage and orient the trocar to mate the trocar to the trocar holding ring in a desired orientation; and
   a controller operatively coupled to the at least one engagement mechanism, the controller configured to determine a position of the trocar relative to the trocar holding ring and to cause the at least one engagement mechanism to engage the trocar when the trocar is determined by the controller to be at a predetermined position relative to the trocar holding ring.

10. The surgical system of claim 9, wherein the trocar holding ring has at least one ring sensor disposed on the trocar holding ring and configured to sense at least one of a position and an orientation of a trocar.

11. The surgical system of claim 10, wherein the trocar has at least one trocar sensor disposed thereon, and wherein the at least one ring sensor is configured to detect a presence of the at least one trocar sensor.

12. The surgical system of claim 11, wherein the at least one trocar sensor comprises a plurality of trocar sensors, and each of the plurality of trocar sensors is configured to emit a distinct signal to facilitate a determination of a relative position of each of the plurality of trocar sensors with respect to the at least one ring sensor.

13. The surgical system of claim 11, wherein the controller is configured to receive data from the at least one trocar sensor relating to at least one of the position and the orientation of the trocar, and to transmit instructions to the electromechanical robotic arm to cause the electromechanical robotic arm to orient the trocar holding ring based on the received data.

14. The surgical system of claim 9, further comprising a depth sensor disposed on the trocar holding ring and a trocar depth sensor disposed on the trocar, the depth sensor and the trocar depth sensor operably coupled to the controller and configured to facilitate a determination, by the controller, of an extent to which a portion of the trocar has extended through the trocar holding ring.

15. The surgical system of claim 9, wherein the at least one engagement mechanism comprises a closure cam movable between a retracted position, in which the closure cam is retracted within the trocar holding ring, and an extended position in which the closure cam is extending from the trocar holding ring, and the engagement of the at least one engagement mechanism includes moving the closure cam between the retracted position and the extended position.

16. The surgical system of claim 9, wherein the at least one engagement mechanism is configured to fit into a complementary recess formed in the trocar.

\* \* \* \* \*